United States Patent [19]

Rappaport

[11] 4,068,651
[45] Jan. 17, 1978

[54] CATALYTIC HEATER OR WARMER

[76] Inventor: Alfred A. Rappaport, 2081 S. Ocean Drive, Apt. 305, Hallandale, Fla.

[21] Appl. No.: 716,260

[22] Filed: Aug. 20, 1976

[51] Int. Cl.$^2$ .............................................. A61F 7/06
[52] U.S. Cl. .................................... 126/208; 431/328
[58] Field of Search ......................... 126/208; 431/328

[56] References Cited

U.S. PATENT DOCUMENTS

| | | | |
|---|---|---|---|
| 1,502,251 | 7/1924 | Kanazawa | 126/208 |
| 2,670,728 | 3/1954 | Smith | 126/208 |
| 2,746,138 | 5/1956 | Smith | 126/208 |
| 2,914,060 | 11/1959 | Wilcox | 126/208 |
| 2,942,601 | 6/1960 | Smith | 126/208 |
| 3,046,975 | 7/1962 | Gottwald | 126/208 |
| 3,049,117 | 8/1962 | Matoba | 126/208 |
| 3,119,650 | 1/1964 | Bilyeu | 126/208 |
| 3,295,510 | 1/1967 | Matoba | 126/208 |
| 3,405,704 | 10/1968 | Wintz | 126/208 |
| 3,420,221 | 1/1969 | Wintz | 126/208 |

Primary Examiner—Ronald C. Capossela

Attorney, Agent, or Firm—Gustave Miller

[57] ABSTRACT

This is a catalytic warmer or heater which may be made in different sizes and shapes. A chimney section top has an opening through which a heatable material container is insertable, and which rests on an X-frame supported on punched-in tongues providing draft apertures for the chimney, while a lower spaced series of punched-in tongues rest on a catalyst containing cage which, in turn, rests on a flange of fuel cartridge section below having a wick extending up from the cartridge to be lighted temporarily to initiate the catalytic combustion process. The supporting X-frame has a depending cylinder providing a snuffer to snuff out the wick and permit the catalytic combustion to continue. The catalytic combustion is stopped when desired by merely turning the entire heater or warmer upside down and then removing the fuel cartridge containing section, now on top, from the chimney section, now on bottom, the catalyst cage remaining with the chimney section and thus separated from the cartridge fuel section.

16 Claims, 8 Drawing Figures

U.S. Patent  Jan. 17, 1978  4,068,651
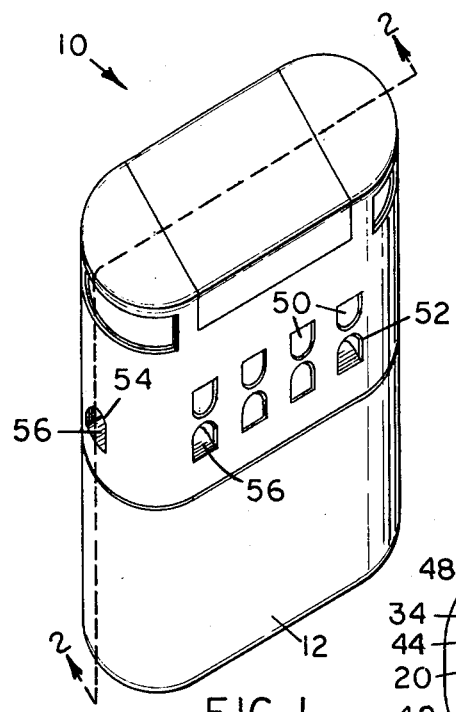
FIG.1
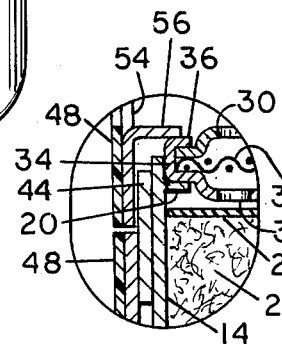
FIG. 2A
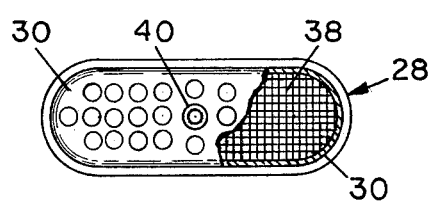
FIG.4
FIG.3
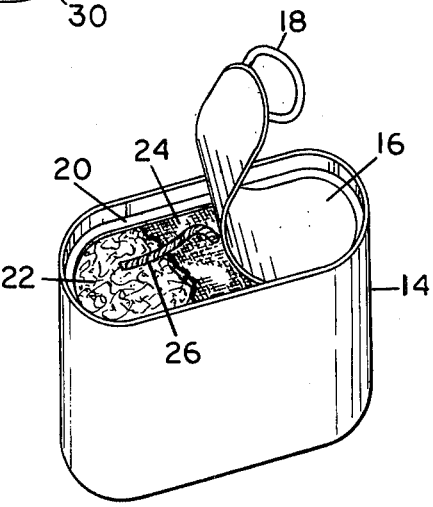
FIG.5
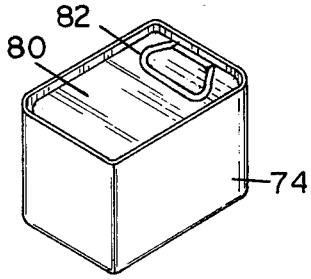
FIG.6
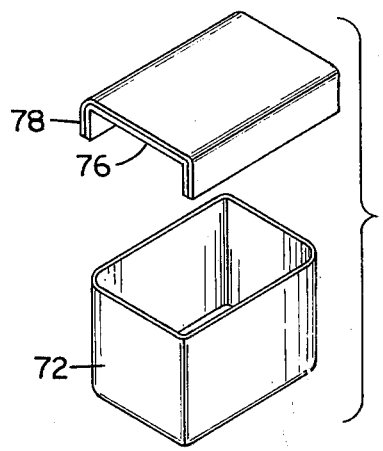
FIG.7

CATALYTIC HEATER OR WARMER

BACKGROUND OF THE INVENTION

Small, pocket size hand warmers and scent propagators are well known, as illustrated in U.S. Pat. Nos. 2,670,728; 2,942,601; 3,049,117; 2,914,060; 3,046,975; 3,119,650; 3,295,510; 3,405,704; and 3,420,221. These all have one feature in common, the fuel must be poured in the absorbent material by the user, with its attending dangers. Too much fuel, there is danger of a fire, and, also, the excess fuel may make the catalytic material inoperative. The first two listed patents to Smith show the now conventional manner of making the catalytic member. There is no provision in any of these patents that they can be used as other than a hand or human body warmer except U.S. Pat. No. 3,119,650, which also discloses using the heat to propagate a scent for attracting wild game.

SUMMARY OF THIS INVENTION

This invention is a catalytic heater or warmer which may be made in different sizes, small, as illustrated in the above prior art, for use as a hand or body warmer; larger, for propagating an insect repellent scent, and still larger for use in warming or heating foods or liquids. It may be made of a size to hold and heat cans of food or liquids as purchased from a grocery-type store, and used in the home, at a picnic, or elsewhere.

This invention consists of a stainless steel upper chimney section removably supported on a lower fuel cartridge receiving stainless steel section and, when put together, hold a catalytic cage member therebetween, both sections being externally insulated to retain heat. The fuel cartridge, a disposable item, is sealed until it is to be used. The sealing cover is removed, leaving an inwardly extending flange, and the cartridge contains a premeasured amount of any suitable ethyl alcohol or other petroleum distillage in a suitable absorbent material, which has a wick depending therein and extendable upwardly therefrom through an activated charcoal impregnated fuel filter on top of the fuel absorbent material.

A catalyst containing cage is supported on a flange left when the sealing cover is removed. This cage consists of a pair of dished foraminous stainless steel plates or screens having connected flanges, and supporting a screen impregnated with a catalyst material such as platinum or palladium, which may be made as set forth in the first two above-mentioned patents, both to Smith, U.S. Pat. Nos. 2,670,728 and 2,942,601. The cage plates and the catalytic screen have aligned apertures to receive the wick extending therethrough, the cage plates having upwardly extending lips to facilitate inserting the wick therethrough.

An inwardly spaced rim is provided at the top of the lower fuel cartridge containing section and snugly and removably fits and supports the upper chimney section thereon. Two rows of punched-in apertures are provided in the lower area of the chimney section. In the lower row, punched-in tongues remain on the bottom of some or all of the holes, and rest on the catalyst cage to hold it in position. In the upper row, punched-in tongues are provided at the top of the holes and provide a support for an X-frame secured thereto, from the bottom of which there depends a closed cylinder to act as a wick snuffer when placed thereover. This X-frame also acts as a support for a heatable material container inserted through the top of the upper chimney section, and a separate insulation coated cover is provided for such container. Otherwise, the top of the upper chimney section is closed and has chimney openings at both sides, through which the products of combustion escape, the punched-in holes provide air draft, and combustion escape openings are provided near the top of the chimney section.

OBJECTS OF THIS INVENTION

It is an object of this invention to provide a catalytic warmer or heater which may be made in several sizes for different purposes.

A further object of this invention is to provide a catalytic heater or warmer which, in appropriate sizes, may be used as a hand or body warmer, an insect repellent propagator, and a food or liquid heater.

A further object of this invention is to provide a safe catalytic heater by providing a disposable fuel cartridge having a premeasured amount of suitable fuel absorbed in a suitable absorbent material.

A further object of this invention is to provide a catalytic warmer wherein the fuel is not poured into the absorbent material by the user with its attendant danger of fire, but is provided in a premeasured disposable sealed cartridge.

A further object of this invention is to provide a catalytic heater or warmer where the danger of fire from spilled fuel is negligible.

A further object of this invention is to provide a disposable fuel cartridge which also includes a fuel vapor filter.

A further object of this invention is to provide a catalytic warmer wherein a fuel wick snuffer is provided for automatically snuffing the wick flame when a chimney section is assembled thereon by the user.

BRIEF DESCRIPTION OF THE FIGURES

With the above and other objects in view, this invention consists in the details of construction and combination of parts, as will be more fully understood from the following description, when read in conjunction with the accompanying drawing, in which:

FIG. 1 is a perspective view of the catalytic warmer or heater of this invention.

FIG. 2 is a vertical sectional view of FIG. 1, on line 2—2 of FIG. 1.

FIG. 2A is an enlarged detail of the circled area in FIG. 2.

FIG. 3 is a section on line 3—3 of FIG. 2.

FIG. 4 is a plan view, partly broken away, of the catalyst cage.

FIG. 5 is a perspective view of the disposable fuel and filter cartridge, partly opened, and with the fuel vapor filter partly broken away.

FIG. 6 is a perspective view of sealed insect repellent or food container, of a size to fit in the chimney section top opening.

FIG. 7 is a perspective view of a heatable material container, similar to that in FIG. 6, but including a cover for use while heating.

DETAILED DESCRIPTION OF THE INVENTION

There is shown at 10 the complete, assembled catalytic heater or warmer of this invention. This heater 10 includes a lower fuel cartridge containing section 12 adapted to receive and hold a disposable fuel cartridge 14. This fuel cartridge 14 has a sealed, readily removable cover 16 having a pull handle 18 so that it can be pulled up, leaving an inwardly extending ledge 20 adjacent but slightly spaced from the top edge of the cartridge. Within the cartridge 14 there is provided a wad of fuel absorbent material 22 which is saturated with a premeasured amount of fuel, just enough so that it will not leak when turned upside down. Any suitable fuel may be used, such as petroleum distillates or ethyl alcohol or other suitable readily vaporizable fuels.

This disposable cartridge 14 will preferably be made of aluminum. On the top of fuel absorbent material 22, there is provided an activated charcoal impregnated screen filter 24 to filter the fuel vapor as it rises therethrough in operation. Extending through this filter 24 is a non-inflammable wick 26 from near its bottom to a suitable distance thereabove, so that it may be extended high enough to pass through appropriate openings through a catalyst containing stainless steel cage 28 placed on and supported on the flange 20 after the fuel cartridge 14 has been opened and inserted in lower section 12.

This stainless steel catalyst cage 28 consists of two flanged or dished foraminated stainless steel plates 30 and 32, the flange 34 of one plate 32 being bent over into a lip 36 over the flange of the other plate for locking the plates 30 and 32 together and also holding a catalyst impregnated screen 38, platinum or palladium being the catalyst material conventionally being used, made up possibly as set forth in the Smith patents listed above, U.S. Pat. Nos. 2,670,728 and 2,942,601. The perforations through the plates 30 and 32 have upwardly extending lips 40 so that the upper end 42 of the wick 26 may be readily extended therethrough.

An inward flange 44 secured at the inner top of the lower section 12 snugly and removably receives and supports an upper stainless steel chimney section 46. Both the lower section 12 and upper section 46 are covered with a suitable plastic, rubber or other heat insulating coating 48. The chimney upper section 46 is provided with two vertically spaced rows on the front and back sides of punched-in air draft apertures 50 and 52, the lower row also having two end apertures 54 in the curved sides of the upper section 46.

Tongues 56 inturned from the bottom of the end apertures 54 and some, but not necessarily all, of the tongues 56 of the bottom row extend over the catalyst cage flange lip 36 to hold the cage 28 in place.

The four end upper row apertures 50 have tongues 58 punched in from the tops of the apertures 50, and provide a support to which the ends of the X-fingers 60 of an X-frame 62 are attached. Depending from the X-crossing of the X-frame 62 is a snuffer inverted cylinder 64 into which the lighted wick 42 will extend when the upper chimney section 46 is placed on the lower fuel cartridge containing section 12, thus snuffing out the wick flame, only after it has been allowed to burn about one and a half minutes, more or less, to initiate the heating of the catalyst impregnated screen 38.

The chimney section 46 has combustion products escape openings 66 cut into it just below its top roof 68 at both ends, the top roof 68 having downwardly extending lips 70 from the sides of a center opening through which a heatable material container 72 or 74 may be snugly inserted. A cover 76, heat insulated at 78, fits snugly over containers 72 or 74, as desired. The container 72 may be used to receive any material that it is desired to heat, which may be liquid or solid, such as food or otherwise as desired. The container 74 is sealed with a cover 80 having a handle 82 for readily removing the cover 78. The container 74 may be a food can, shaped and sized to fit through the chimney roof 68 to rest on the X-frame 62. Also, it may be used to propagate any desirable vapor, whether insect repellent or otherwise, one example of which is commercially known as "Deet", but any other suitable vapor may be used.

OPERATION OF THE INVENTION

In operation, a fuel cartridge 14 is inserted in the lower section 12 after its cover 16 has been removed by pulling its handle 18. The upper end 42 of the wick 26 is then extended up through the aperture lips 40 of catalyst cage 28 as the cage 28 is placed down over the flange 20. Then the wick is lit with a flaming match, or otherwise, and allowed to burn for about a minute and a half, more or less, until the catalyst material shows a red glow, thus serving to ignite the vapors rising from the fuel impregnated material 22 through the activated charcoal filter screen 24 to remove any undesirable irritants that could be toxic to the user.

Next, the chimney section 46 is placed thereover onto the inner rim flange 44, with the aperture tongues 56 resting on the cage flange lip 36 thus holding the cage 28 in position, and simultaneously the cylinder 64 will snuff out the flame on the wick 42. The container 72 or 74 of the desired heatable material is then placed down through the roof top 68 between the chimney section lips 70 to rest on the X-frame 62 and be covered, if desired, by the cover 76, or left open, if propagating insect repellent. Obviously, the insect repellent may be absorbed in similar absorbent material within container 74 so that it will not spill over.

To stop the action of the heater 10, the entire heater 10 is turned upside down, and the fuel cartridge section 14 now on top is lifted off, thus separating the fuel cartridge 14 from the catalyst cage 28, and the catalyst cage cools off, after which it may be reassembled for storage until next needed for use.

The heater 12 may be made in any desired size, from a pocket or hand warmer size to a camp or home food heater, to receive and heat commercially prepared containers of food of the desired size, or to receive any container of the proper size.

The term "foraminated" as used in this specification and its claims means any article with some holes therethrough, whether it be a screen of any suitable material or a plate with holes formed therethrough. Thus, a metal plate with holes therethrough, or a metal or plastic screen, are both "foraminated" within the scope of this disclosure and its claims.

ABSTRACT OF THE DRAWING

In the drawing, like numbers refer to like parts, and for the purpose of explication set forth below are the numbered parts of the improved CATALYTIC WARMER OR HEATER of this invention.

10 catalytic heater and warmer
12 lower section
14 disposable fuel cartridge
16 sealed, removable cartridge cover
18 pull handle on 16
20 ledge adjacent top of 16
22 fuel absorbent material in 16
24 activated charcoal impregnated screen vapor filter
26 wick
28 catalyst containing cage 30 top cage stainless steel plate
32 lower cage stainless steel plate
34 flange of plate 32
36 bent over lip of 34
38 catalyst impregnated screen
40 upwardly extending apertured lips through which wick upper end 42 extends
42 wick upper end
44 inward flange at top of 12
46 chimney upper section
48 heat insulating coating on 12 and 46
50 upper air draft apertures
52 lower air draft apertures
54 end apertures of lower row of apertures 52
56 inturned tongues at bottom of punched-in apertures 52 and 54
58 tongues punched in from top of aperture 50
60 X-fingers supported on 58
62 X-frame
64 depending snuffer cylinder
66 combustion products chimney escape openings
68 top roof of chimney section 46
70 downwardly extending lips in 68
72 heatable material container through opening between lips 70 in 68
74 sealed heatable material container
76 cover for 72
78 insulating material on 76
80 sealed cover of 74
82 handle for removing cover 80

Although the invention has been described in detail, such description is intended as being illustrative rather than limiting, since the invention may be variously embodied.

Having thus disclosed the nature of this invention, what is claimed is:

1. A catalytic heater (10) comprising a lower container section (12) having an upwardly extending flange (44) adjacent to the top of said lower container section (12), an upper chimney section (46) fitting snugly on and removably supported on said lower container section (12) about said lower container section extending flange (44), said chimney section (46) having air draft means (50, 52, 54) therein, a sealed fuel cartridge (14) having a fuel absorbent material (22) therewithin having a premeasured amount of liquid fuel absorbed therein, and a wick (26) in said fuel absorbent material (22) extending up from said material (22), said sealed fuel cartridge (14) having a readily removable cover (16) secured thereon, said cartridge fitting within said lower container section (12), a catalyst containing member (28) supported over said fuel absorbent material (22) and having aperture means (40) through which said wick (26) is extended, a wick snuffer (64) depending from a frame (62) mounted above said fuel cartridge (14) insertable through a top opening in the roof (68) of said chimney section (46), said chimney section having fuel combustion vapor emitting openings (66) therein.

2. The heater of claim 1, said air draft means comprising a plurality of apertures (50, 52, 54) in the lower portion of said chimney section.

3. The heater of claim 2, said apertures (50, 52, 54) extending about said chimney section (46), and tongues (56, 58) extending inwardly from said apertures, said cartridge (14) having an inwardly extending ledge (20) remaining adjacent its top edge when the sealing cover (16) is removed, said catalyst containing member (28) being supported on said ledge (20) over said opened cartridge (14), at least some of said tongues holding said catalyst containing member down on said ledge (20).

4. The heater of claim 3, and an X-frame (62) with its X-fingers (60) secured on some of said tongues, said fingers (60) permitting access of the fuel combustion vapor to said heatable container (72 or 74).

5. The heater of claim 4, said plurality of apertures being in two vertically spaced rows, some of said tongues (56) extending inwardly from the bottom of the apertures (52, 54) of the lower row of apertures holding down said catalyst containing member (28) in position on said ledge (20).

6. The heater of claim 5, others of said tongues (58) extending inwardly from the top of the apertures (50) of the upper row of apertures providing support for said heatable container supporting X-frame (62).

7. The heater of claim 1, said snuffer (64) comprising an inverted stainless steel hollow cylinder.

8. The heater of claim 1, said catalyst containing member comprising a foraminated cage (28) having a catalyst impregnated foraminated member (38) therewithin.

9. The heater of claim 8, said cage (28) comprising two dished foraminated stainless steel plates (30, 32) having flanges (34, 36) joined together and said catalyst impregnated member comprising a foraminated screen.

10. The heater of claim 8, said foraminated cage member (28) and said catalyst member (38) having said aligned openings through which said wick (42) is extended, said foraminated cage member (28) wick openings having upwardly extending lip guides (40) thereabout for guiding said wick (42) therethrough.

11. The heater of claim 1, and a cover (76) for closing said heatable material container (72 or 74) fitting thereover through a suitable opening in the top (68) of said chimney section (46).

12. The heater of claim 11, said upper (46) and lower (12) sections and said cover (74) being coated with a heat retaining material (48, 78).

13. The heater of claim 1, and a fuel vapor filter (24) supported above said fuel supply (22).

14. The heater of claim 13, said filter comprising activated charcoal.

15. The heater of claim 13, said filter (24) being between said catalyst cage member (28) and said fuel supply (22).

16. The heater of claim 1, said heatable material container (72, 74) having a cover (76) and containing vapor producing material.

* * * * *